US009782773B2

(12) United States Patent
Astier et al.

(10) Patent No.: US 9,782,773 B2
(45) Date of Patent: Oct. 10, 2017

(54) NANOGAP STRUCTURE FOR MICRO/NANOFLUIDIC SYSTEMS FORMED BY SACRIFICIAL SIDEWALLS

(71) Applicant: International Business Machines Corporation, Armonk, NY (US)

(72) Inventors: Yann A. Astier, Irvington, NY (US); Markus Brink, White Plains, NY (US); Michael F. Lofaro, Brookfield, CT (US); Joshua T. Smith, Croton on Hudson, NY (US)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 43 days.

(21) Appl. No.: 14/950,320

(22) Filed: Nov. 24, 2015

(65) Prior Publication Data
US 2017/0043339 A1 Feb. 16, 2017

Related U.S. Application Data

(63) Continuation of application No. 14/824,518, filed on Aug. 12, 2015.

(51) Int. Cl.
*H01L 21/311* (2006.01)
*B01L 3/00* (2006.01)
(Continued)

(52) U.S. Cl.
CPC ... *B01L 3/502707* (2013.01); *B01L 3/502753* (2013.01); *B01L 3/502761* (2013.01);
(Continued)

(58) Field of Classification Search
CPC ............ B81C 1/00063; B81C 1/00087; B81C 1/00103; G01N 27/3278; H01L 21/30617
(Continued)

(56) References Cited

U.S. PATENT DOCUMENTS

2012/0322259 A1\* 12/2012 Liu ..................... B81C 1/00063
438/666
2013/0115775 A1\* 5/2013 O'Brien ............ H01L 21/31111
438/702

(Continued)

OTHER PUBLICATIONS

List of IBM Patents or Patent Applications Treated as Related; Date Filed: Nov. 24, 2015, p. 1-2.
(Continued)

*Primary Examiner* — Binh X Tran
(74) *Attorney, Agent, or Firm* — Cantor Colburn LLP; Vazken Alexanian

(57) ABSTRACT

A technique relates to a nanogap array. A substrate has been anisotropically etched with trenches that have tapered sidewalls. A sacrificial layer is on bottoms and the tapered sidewalls of the trenches. A filling material is formed on top of the sacrificial layer in the trenches. Nanogaps are formed where at least a portion of the sacrificial layer has been removed from the tapered sidewalls of the trenches while the sacrificial layer remains on the bottoms of the trenches. Each of the nanogaps is formed between one tapered sidewall of the substrate and a corresponding tapered sidewall of the filling material. The one tapered sidewall of the substrate opposes the corresponding tapered sidewall. A capping layer is disposed on top of the substrate and the filling material, such that the nanogaps are covered but not filled in.

10 Claims, 15 Drawing Sheets

(51) Int. Cl.
*B81C 1/00* (2006.01)
*B24B 37/04* (2012.01)
*G01N 27/447* (2006.01)
*G01N 33/487* (2006.01)
*G01N 30/74* (2006.01)
*G01N 30/60* (2006.01)
*G01N 30/88* (2006.01)

(52) U.S. Cl.
CPC ........ *B24B 37/042* (2013.01); *B81C 1/00087* (2013.01); *G01N 27/44791* (2013.01); *G01N 33/48721* (2013.01); *B01L 2200/0652* (2013.01); *B01L 2200/12* (2013.01); *B01L 2300/0681* (2013.01); *B01L 2300/0858* (2013.01); *B01L 2300/0887* (2013.01); *B01L 2300/0896* (2013.01); *B81C 2201/013* (2013.01); *B81C 2201/0104* (2013.01); *G01N 30/6039* (2013.01); *G01N 30/74* (2013.01); *G01N 2030/885* (2013.01)

(58) Field of Classification Search
USPC .................. 438/696, 700, 701, 702, 753
See application file for complete search history.

(56) References Cited

U.S. PATENT DOCUMENTS

| | | | |
|---|---|---|---|
| 2013/0221483 A1* | 8/2013 | Popp | H01L 28/90 257/532 |
| 2015/0263083 A1* | 9/2015 | Popp | H01L 28/90 257/532 |

OTHER PUBLICATIONS

Yann A. Astier, et al., "Nanogap Structure for Micro/nanofluidic Systems Formed by Sacrificial Sidewalls", U.S. Appl. No. 14/824,518, filed Aug. 12, 2015.

* cited by examiner

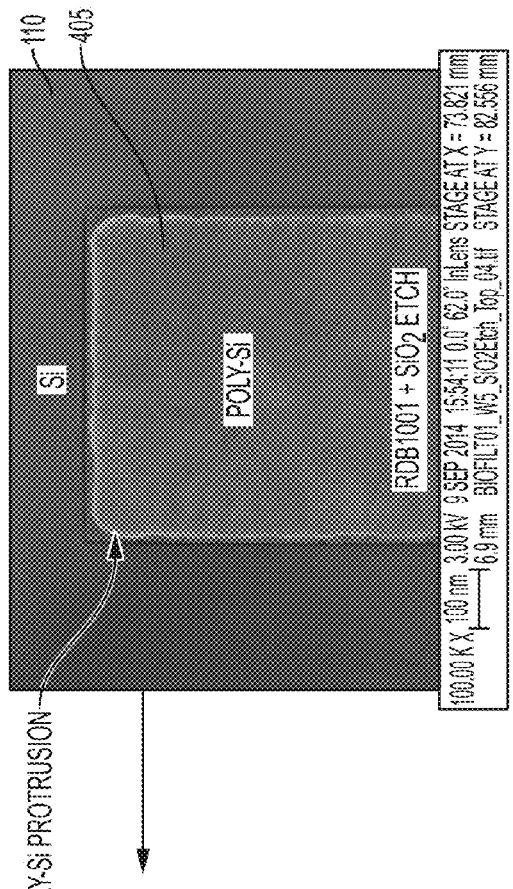
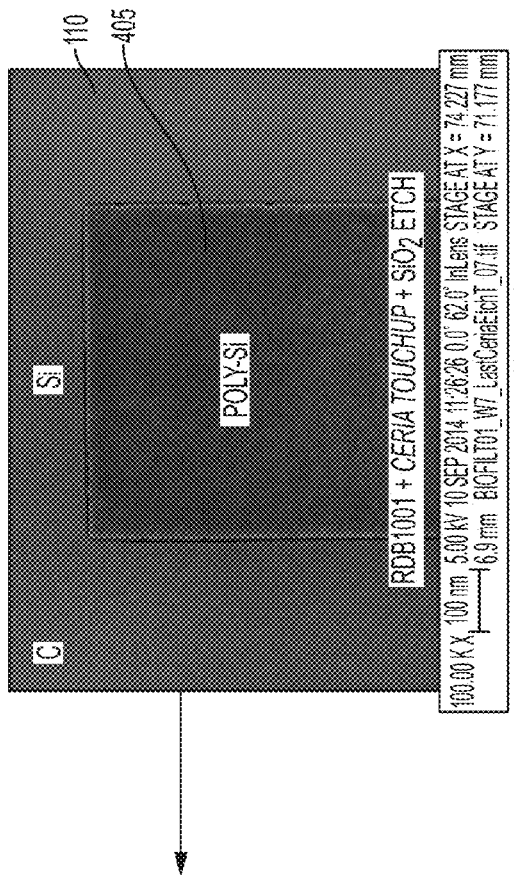
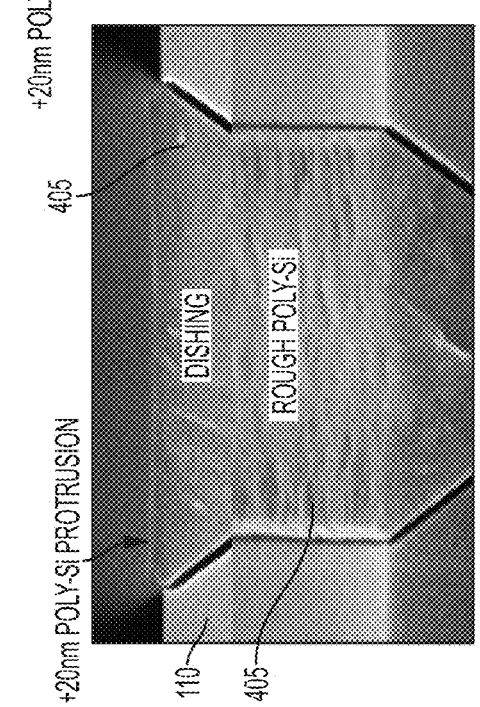
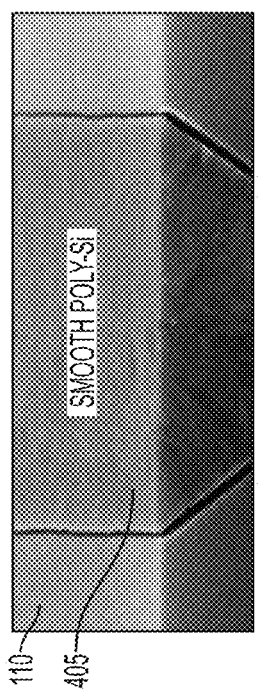
FIG. 6B-1  FIG. 6B-2  FIG. 6B-3  FIG. 6B-4

PATTERN WINDOWS IN A HARD MASK LAYER DISPOSED ON A SUBSTRATE  1005

↓

ANISOTROPICALLY ETCH TRENCHES IN THE SUBSTRATE ACCORDING TO THE WINDOWS PATTERNED IN THE HARD MASK LAYER, SUCH THAT THE TRENCHES HAVE TAPERED SIDEWALLS  1010

↓

FORM A SACRIFICIAL LAYER ON BOTTOMS AND THE TAPERED SIDEWALLS OF THE TRENCHES  1015

DISPOSE A FILLING MATERIAL IN THE TRENCHES AND ON TOP OF THE HARD MASK LAYER, THE FILLING MATERIAL BEING ON TOP OF THE SACRIFICIAL LAYER IN THE TRENCHES  1020

PERFORM A FIRST CHEMICAL MECHANICAL POLISHING TO REMOVE THE FILLING MATERIAL DOWN TO THE HARD MASK LAYER, THE FIRST CHEMICAL MECHANICAL POLISHING CONFIGURED TO STOP ON THE HARD MASK LAYER SUCH THAT THE TRENCHES REMAINED FILLED WITH THE FILLING MATERIAL  1025

PERFORM A SECOND CHEMICAL MECHANICAL POLISHING TO REMOVE THE HARD MASK LAYER, THE SECOND CHEMICAL MECHANICAL POLISHING REMOVING DISHING AND ROUGHNESS ASSOCIATED WITH THE FILLING MATERIAL IN THE TRENCHES AFTER THE FIRST CHEMICAL MECHANICAL POLISHING 1030

REMOVE AT LEAST A PORTION OF THE SACRIFICIAL LAYER FROM THE TAPERED SIDEWALLS OF THE TRENCHES SUCH THAT NANOGAPS ARE FORMED WHERE THE SACRIFICIAL LAYER IS REMOVED, WHILE THE SACRIFICIAL LAYER REMAINS ON THE BOTTOMS OF THE TRENCHES, WHEREIN EACH OF THE NANOGAPS ARE FORMED BETWEEN ONE TAPERED SIDEWALL OF THE SUBSTRATE AND A CORRESPONDING TAPERED SIDEWALL OF THE FILLING MATERIAL, THE ONE TAPERED SIDEWALL OF THE SUBSTRATE OPPOSING THE CORRESPONDING TAPERED SIDEWALL 1035

DISPOSE A CAPPING LAYER ON TOP OF THE SUBSTRATE AND THE FILLING MATERIAL, SUCH THAT THE NANOGAPS ARE COVERED BUT NOT FILLED IN 1040

NANOGAP STRUCTURE FOR MICRO/NANOFLUIDIC SYSTEMS FORMED BY SACRIFICIAL SIDEWALLS

DOMESTIC PRIORITY

This application is a continuation of U.S. patent application Ser. No. 14/824,518, filed Aug. 12, 2015, the disclosure of which is incorporated by reference herein in its entirety.

BACKGROUND

The present invention relates to a nanogap structure, and more specifically, to creating nanogaps utilizing sacrificial sidewalls.

The separation and sorting of biological entities, such as cells, proteins, deoxyribonucleic acid (DNA), ribonucleic acid (RNA), etc., is important to a vast number of biomedical applications including diagnostics, therapeutics, cell biology, and proteomics.

Protein and DNA/RNA separation for analytical purposes is traditionally done by gel electrophoresis, where a protein mix is subjected to a strong electric field (typically 30 volts per centimeter (V/cm)). Proteins or DNA/RNA move through the gel at a rate depending on their size and surface charge. The gels are prepared from agarose or acrylamide polymers that are known to be toxic. The outcome of the electrophoresis experiment is revealed optically from staining the proteins with dye, or staining the DNA/RNA with ethidium bromide which is extremely carcinogenic. Gels require sufficient quantities of material for the outcome of the electrophoresis to be detectable, but bad cross-linking in the gel matrix often leads to inconclusive results and the complete loss of the samples. If the gel matrix size is not adapted to the sample molecule size or if the electrophoresis is left to run for too long, the sample is also lost.

For separation of macromolecules, such as DNA, RNA, proteins, and their fragments, gel electrophoresis is widely employed. Gel electrophoresis currently has a market with world-wide sales greater than $1 billion dollars per year. Gel electrophoresis applied to medical diagnostic represents a multibillion dollar market.

In comparison with traditional techniques, silicon (Si) nanofabrication technology offers much more precise and accurate control in nano-structural dimensions and positioning of the same, and thus can lead to reliable sorting of particles based on their sizes. To date, Si-based Lab-on-a-Chip approaches using Si pillars arrays have shown promise. However, only sorting in the micron ($10^6$ or micrometer (μm)) range has been demonstrated using these techniques, which does not access the nanometer dimensions required for sorting DNA, proteins, etc.

SUMMARY

According to one embodiment, a method for nanogap creation is provided. The method includes patterning windows in a hard mask layer disposed on a substrate, anisotropically etching trenches in the substrate according to the windows patterned in the hard mask layer, such that the trenches have tapered sidewalls, and forming a sacrificial layer on bottoms and the tapered sidewalls of the trenches. The method includes disposing a filling material in the trenches and on top of the hard mask layer, where the filling material is on top of the sacrificial layer in the trenches, and performing a first chemical mechanical polishing to remove the filling material down to the hard mask layer, where the first chemical mechanical polishing is configured to stop on the hard mask layer such that the trenches remained filled with the filling material. Also, the method includes performing a second chemical mechanical polishing to remove the hard mask layer, where the second chemical mechanical polishing removes dishing and roughness associated with the filling material in the trenches after the first chemical mechanical polishing, removing at least a portion of the sacrificial layer from the tapered sidewalls of the trenches such that nanogaps are formed where the sacrificial layer is removed, while the sacrificial layer remains on the bottoms of the trenches. Each of the nanogaps are formed between one tapered sidewall of the substrate and a corresponding tapered sidewall of the filling material, where the one tapered sidewall of the substrate opposes the corresponding tapered sidewall. The method further includes disposing a capping layer on top of the substrate and the filling material, such that the nanogaps are covered but not filled in.

According to one embodiment, a nanogap array is provided. The nanogap array includes a substrate having been anisotropically etched with trenches that have tapered sidewalls, a sacrificial layer on bottoms and the tapered sidewalls of the trenches, and a filling material formed in the trenches, where the filling material is on top of the sacrificial layer in the trenches. The nanogap array includes nanogaps formed where at least a portion of the sacrificial layer has been removed from the tapered sidewalls of the trenches while the sacrificial layer remains on the bottoms of the trenches. Each of the nanogaps are formed between one tapered sidewall of the substrate and a corresponding tapered sidewall of the filling material, where the one tapered sidewall of the substrate opposing the corresponding tapered sidewall. The nanogap further includes a capping layer disposed on top of the substrate and the filling material, such that the nanogaps are covered but not filled in.

Additional features and advantages are realized through the techniques of the present invention. Other embodiments and aspects of the invention are described in detail herein and are considered a part of the claimed invention. For a better understanding of the invention with the advantages and the features, refer to the description and to the drawings.

BRIEF DESCRIPTION OF THE DRAWINGS

The subject matter which is regarded as the invention is particularly pointed out and distinctly claimed in the claims at the conclusion of the specification. The forgoing and other features, and advantages of the invention are apparent from the following detailed description taken in conjunction with the accompanying drawings in which:

FIG. 6B-1 is a scanning electron microscope image illustrating dishing with protrusions of filling material to be removed according to an embodiment;

FIG. 6B-2 is a scanning electron microscope image illustrating line edge roughness and dishing to be removed according to an embodiment;

FIG. 6B-3 is a scanning electron microscope image illustrating removal of the dishing and line edge roughness according to an embodiment;

FIG. 6B-4 is a scanning electron microscope image illustrating removal of the dishing and line edge roughness according to an embodiment;

FIG. 7B-1 is a cross-sectional view of a scanning electron microscope image illustrating that the nanogap has a uniform width along its length according to an embodiment;

FIG. 7B-2 is a perspective view of a scanning electron image partially illustrating the top of the nanogap and the front face of the structure according to an embodiment;

FIGS. 10A and 10B together are a flow chart illustrating a method for nanogap/nanochannel creation according to an embodiment.

DETAILED DESCRIPTION

Figure 1A:
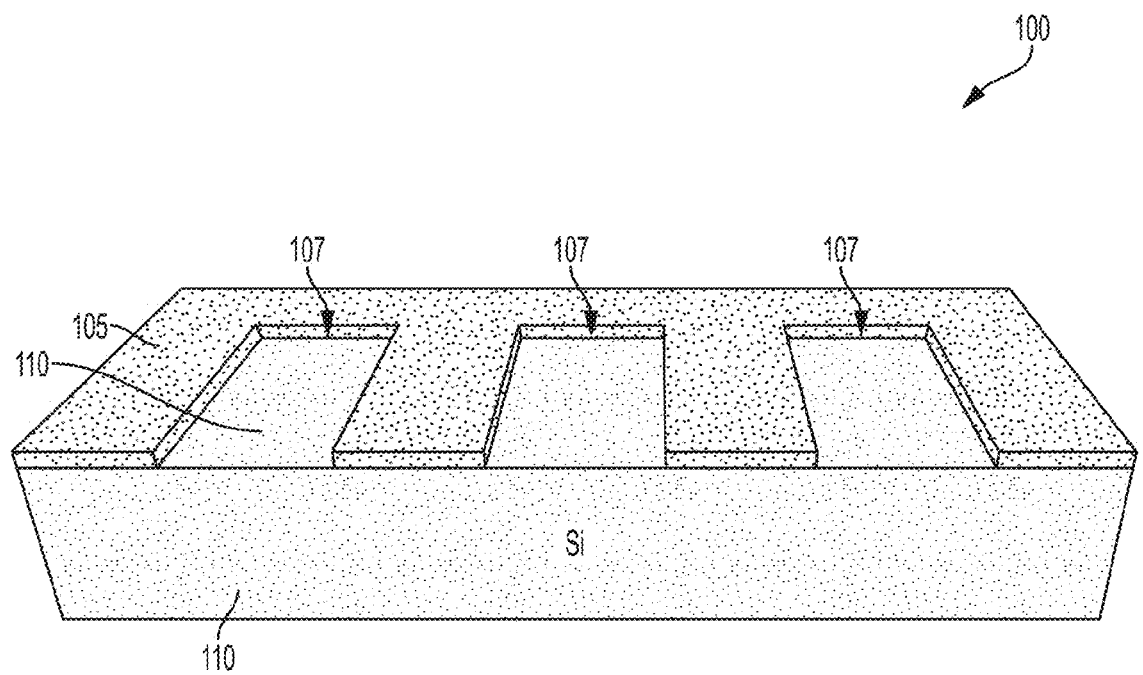
FIG. 1A is a perspective view illustrating an intermediate structure having a patterned hard mask layer on a substrate according to an embodiment.

The sorting of biological polymers, including DNA, RNA, and proteins, is important to a vast number of biomedical applications including diagnostics, therapeutics, cell biology, and proteomics. Accurate and inexpensive sorting and manipulation of individual biomolecules, e.g., nucleic acids, proteins, etc., is central to the understanding of many scientific and biomedical applications. Having a high-throughput and robust device to sort and probe such molecules, according to their specific properties, is beneficial. Current bio-molecular sorting technologies based on gel electrophoresis lack precise control of pore sizes and positions in gels. Biopolymer separation for analytical purposes is traditionally done by gel electrophoresis, where the sample mix moves through the gel under a strong electric field and separates due to their mobility difference depending on their size and surface charge. This state-of-the-art approach has several limitations: (1) the gels are usually made from toxic chemicals such as agarose or acrylamide polymers, (2) the experiment results should be revealed optically by staining the samples with carcinogenic fluorescent dyes such as ethidium bromide, (3) a large amount of material is required to produce the outcome of the electrophoresis, and (4) inconclusive results and complete sample loss can happen due to bad cross-linking in the gel or poor timing control.

In comparison, silicon (Si) nanofabrication technologies offer much more precise and accurate control in nanostructural dimensions and positions with high reproducibility with single molecule precision, and thus can lead to reliable sorting and identification of particles based on their physical properties. The Si-based Lab-on-a-Chip approaches also allow minimal use of the biological sample, multiplexed detection, and possible recovery of samples.

In addition to sorting technology limitations, existing nanochannel architectures for manipulation of nucleic acids are limited in dimensions to 30 (nanometer) nm width (in the state-of-the-art), which is not sufficient to fully stretch nucleic acid chains. Stretching is a feature to read these molecules. Further reliably scaled nanochannels would permit full stretching of these molecules.

Embodiments are applicable to fluidic chips that require manipulation of single molecules (e.g., DNA) via the creation of highly uniform nanogaps and/or nanochannels with widths tunable down 1 nm and up to as high as a few hundred nanometers. Uniform nanogaps are formed in pairs by depositing or growing sacrificial material on the sidewalls of silicon trenches that can be etched away after the trenches have been back filled with a material and polished coplanar with the silicon surface. By fabricating arrays of these nanogaps side-by-side, sealed nanochannel arrays (that can linearize DNA up to 100% of their contour length and/or nanoscale size for filtering molecules using size exclusion dynamics) can be fabricated using this structure to enable new applications not accessible to existing technologies or methods. Particularly, the use of a sacrificial layer rather than lithography to define the gap enables a low-cost, high-throughput, and reproducible route for creating this nanochannel array structure. Note that nanogap, gap, and/or nanochannel may be utilized interchangeably to refer to nanometer size openings.

Sealed gaps with controlled nanoscale dimensions are formed in a fabrication process discussed below. Details regarding each process are discussed along with alternative suggested fabrication methods.

Figure 2:
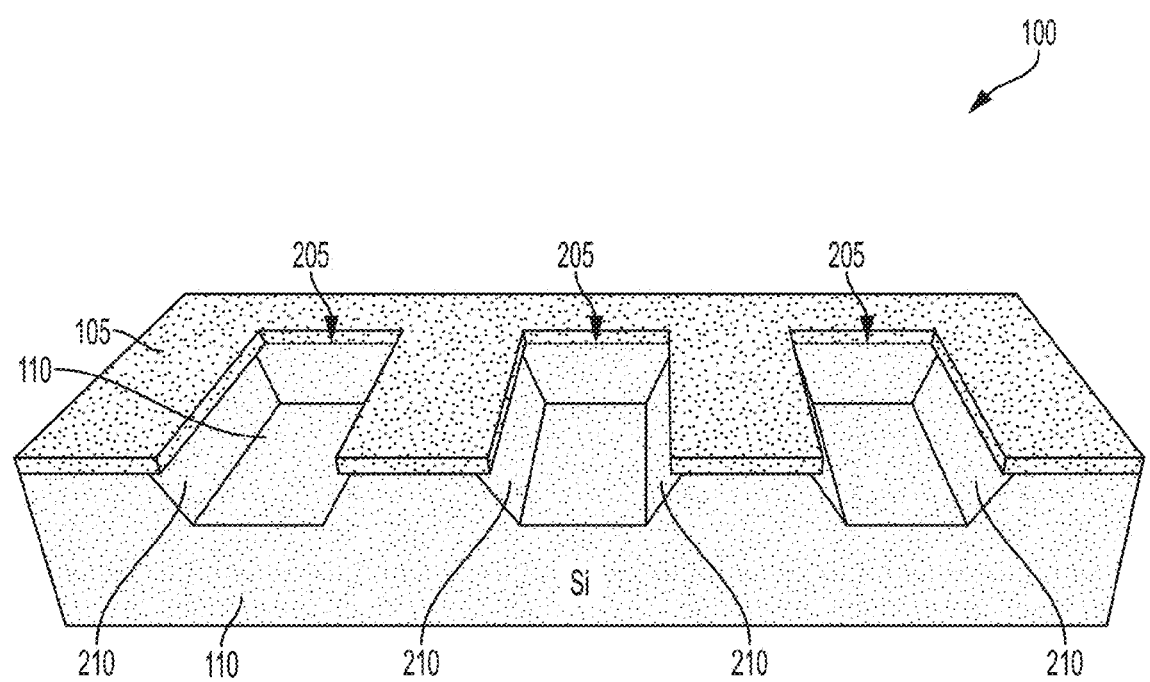
FIG. 2 is a perspective view of the intermediate structure illustrating that tranches are formed in the substrate according to an embodiment.
Figure 3:
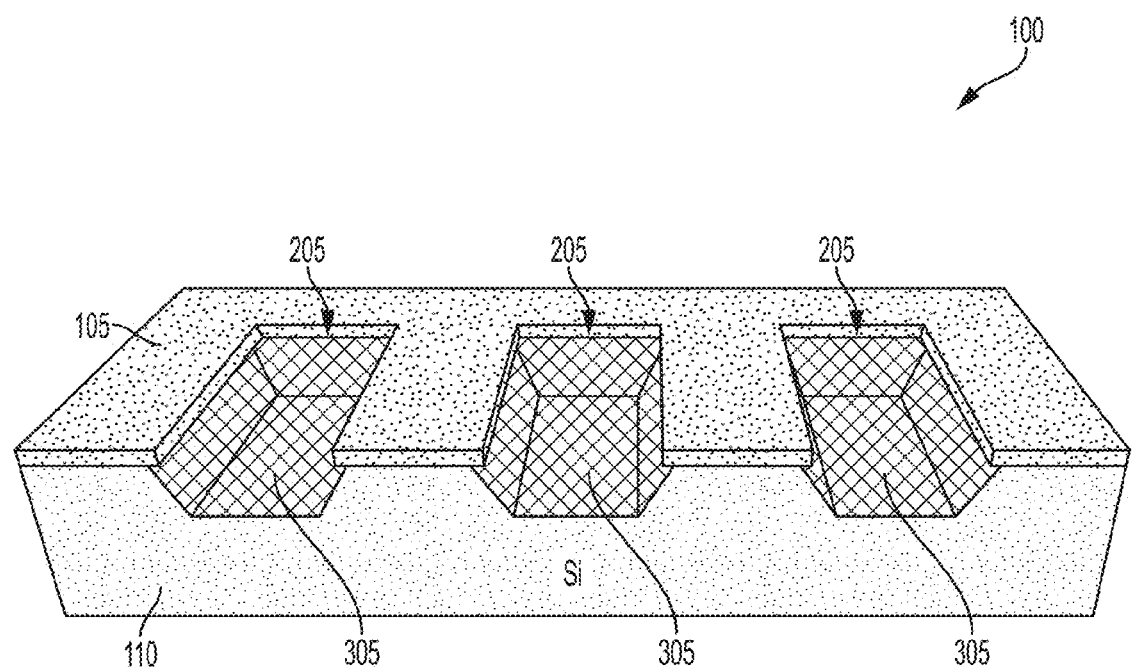
FIG. 3 a perspective view of the intermediate structure illustrating that a sacrificial layer is grown in the trenches to define the gap width of nanogaps according to an embodiment.
Figure 4:
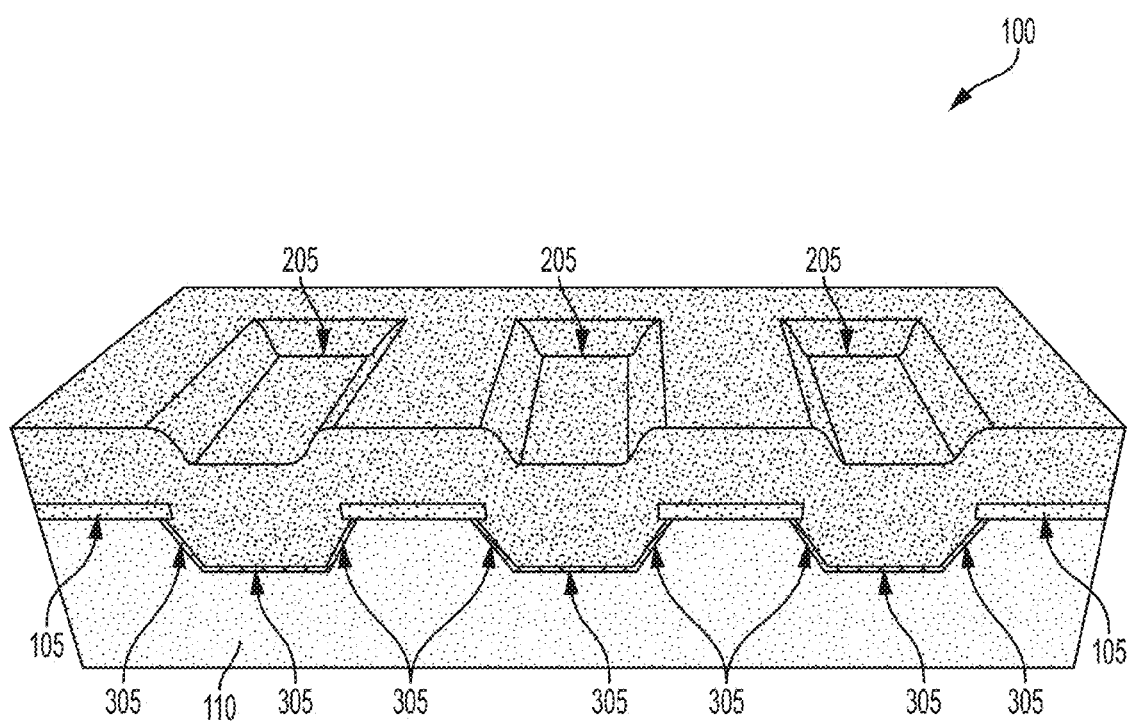
FIG. 4 is a perspective view of the intermediate structure illustrating that the trenches are filled in with a filling material according to an embodiment.
Figure 5:
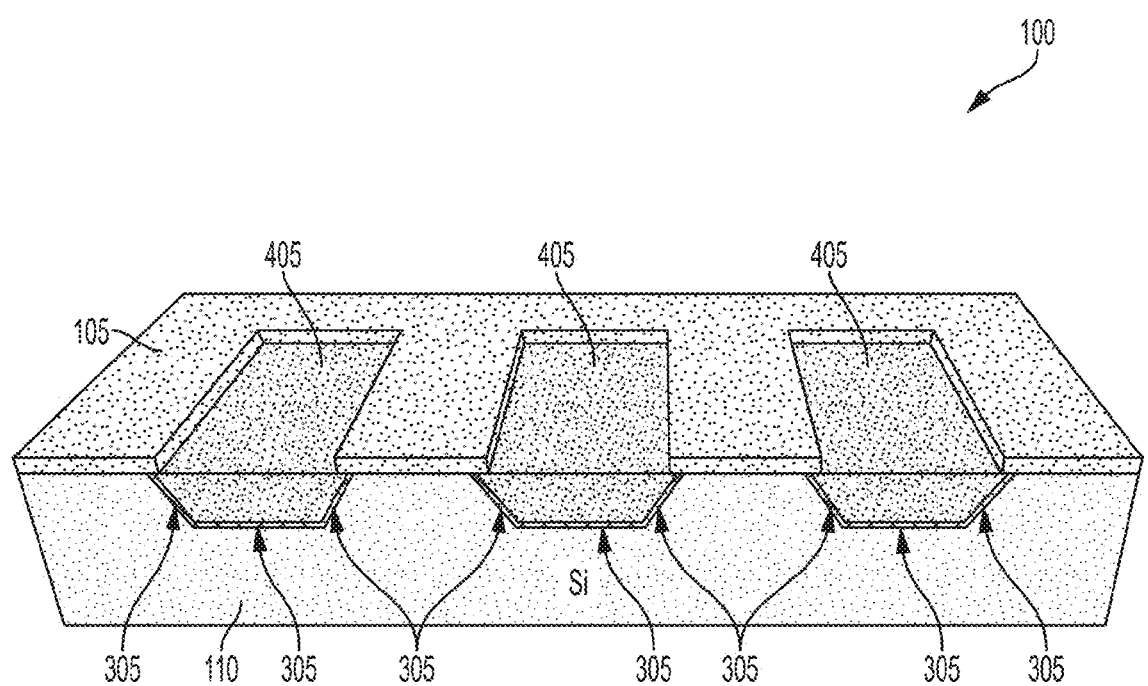
FIG. 5 is a perspective view of the intermediate structure illustrating a first chemical mechanical polishing process according to an embodiment.
Figure 7A:
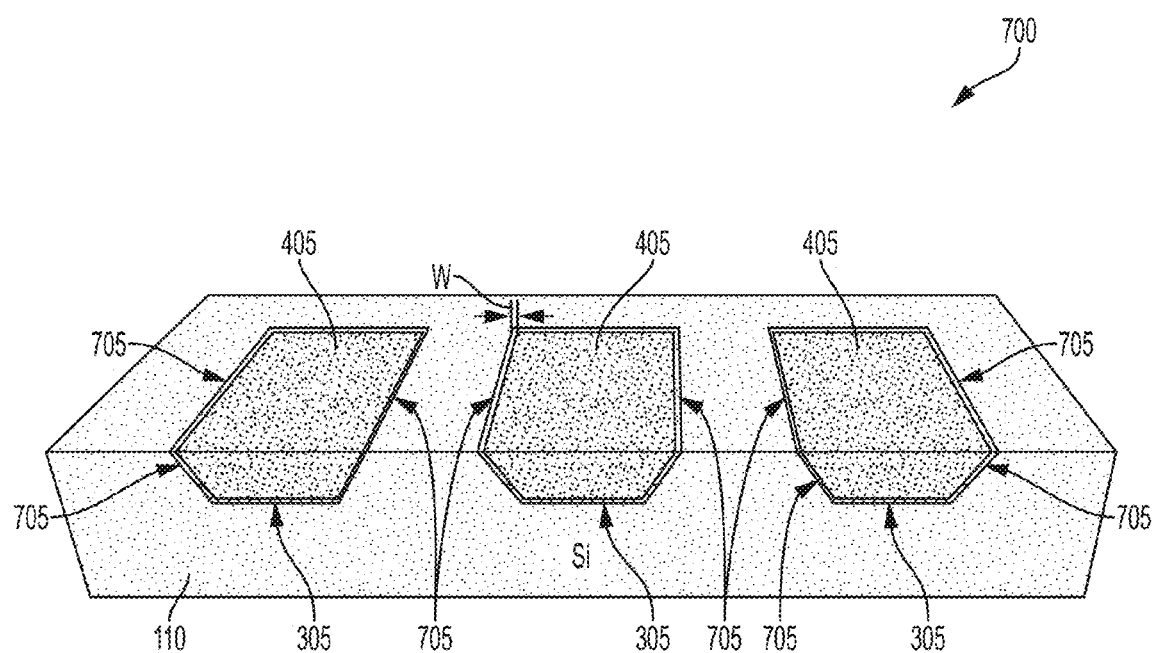
FIG. 7A is a perspective view of the nanochannel/nanogap array structure with the sacrificial layer removed to form the array of nanochannels/nanogaps according to an embodiment.

According to an embodiment, the nanochannel structure, when made by anisotropic wet etch of the Si via tetramethylammonium hydroxide (TMAH) or potassium hydroxide (KOH) etchants, employs two beneficial features for creating pristine nanogaps with highly controlled widths over arbitrary distances. The following is a high-level overview of the fabrication process. First, the fabrication process utilizes anisotropic wet etch techniques described herein to self-limit the lateral Si etch rate to the (111) plane in (100) oriented Si wafers. This means that the walls and floors of the Si trenches etched fall on specific Si planes, enabling atomically smooth sidewall surfaces as a starting foundation for the nanogap structure (as depicted in FIG. 2). Therefore, the anisotropic wet etch techniques correct for any line edge roughness created during lithographic definition of the trench width in the hard mask layer. Second, fabrication process employs deposition or growth techniques, as opposed to lithography, to form the sacrificial material that conformally coats the walls of the trenches to define the gap width (as depicted in FIG. 3). Because deposition techniques can be controlled with nanometer or even sub-nanometer precision (e.g., atomic layer deposition (ALD)), the gap size can be scaled to a regime not accessible by even the most sophisticated and expensive lithography systems on the market. With such a smooth starting surface, polysilicon (poly-Si) deposition on the opposite side of the sacrificial material mirrors the Si face of the sidewalls (as depicted in FIGS. 4 and 5), creating a pristine nanogap when the sacrificial layer is etch away following CMP polishing (as depicted in FIGS. 7A, 7B-1, and 7B-2). The angled orientation of the gap also permits the deposition of a capping layer to seal the nanostructure for microfluidic/nanofluidic applications without filling the gap back up (as depicted in FIGS. 8A, 8B, 8C).

Arrays of the nanogap structures can be fabricated in parallel using standard and inexpensive photolithography techniques. Once the arrays have been produced, reservoirs can be formed by etching through the ends of each trench using reactive-ion etching (RIE). These reservoirs may contain patterned structures necessary for enabling specific applications. For example, prestretching nanopillar features could be patterned in these reservoirs to reduce the entropic barrier for DNA to reduce clogging at the nanogap (i.e. nanochannel) entrance.

FIGS. 1-8 illustrate views of an exemplary fabrication process of forming a nanochannel/nanogap array structure. Now turning to the figures, FIG. 1A is a perspective view illustrating an intermediate structure 100 according to an embodiment. A hard mask (HM) layer 105 is grown or deposited on a substrate 110. In one implementation, the substrate 110 may be bulk silicon (Si), a silicon wafer, etc. The hard mask 105 may be silicon dioxide ($SiO_2$) and/or silicon nitride ($Si_3N_4$). Windows 107 are patterned/opened into the hard mask 105 using standard lithography processes in combination with wet or reactive-ion etching (RIE). The windows 107 are utilized to form trenches as discussed herein.

Figure 1B:
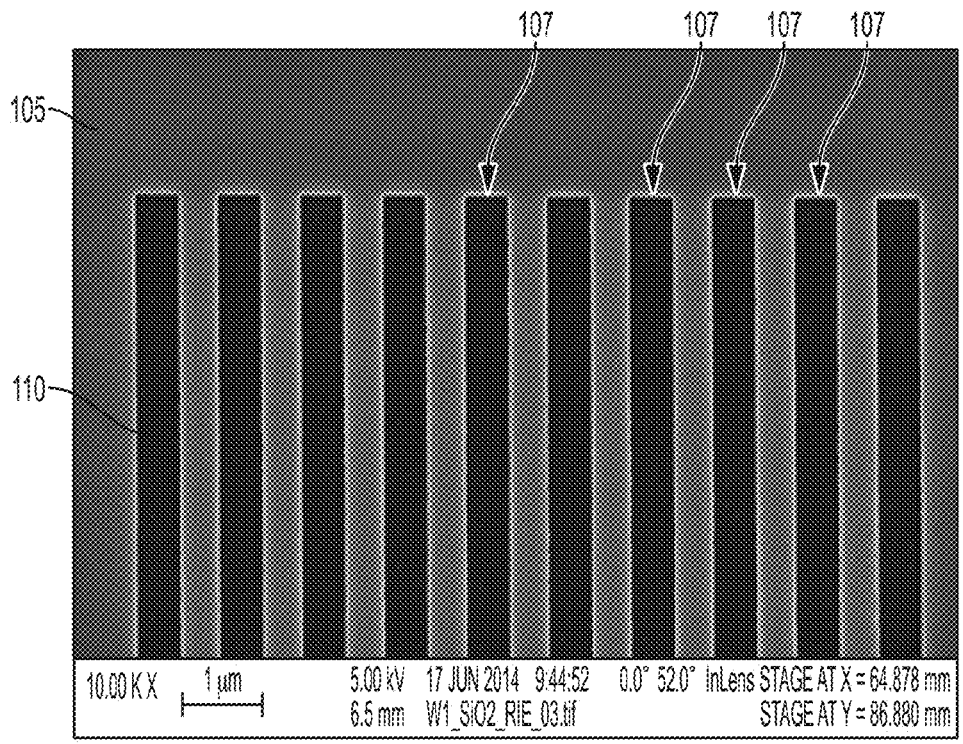
FIG. 1B is a scanning electron microscope image of the intermediate structure according to an embodiment.
Figure 1C:
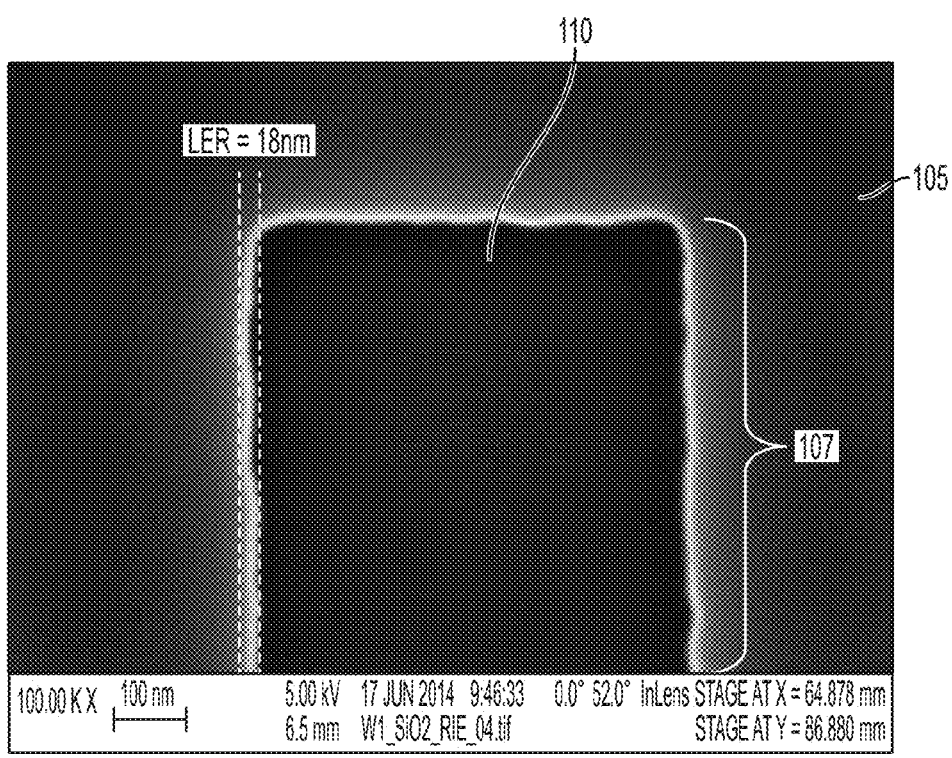
FIG. 1C is a zoomed in view of the scanning electron microscope image of the intermediate structure according to an embodiment.

FIGS. 1B and 1C are scanning electron microscope (SEM) images. FIG. 1B is a top-down SEM image showing e-beam lithography defined rectangular windows 107 etched into, e.g., a 50 nm thermally grown $SiO_2$ hard mask 105. Standard $SiO_2$ RIE-based etch chemistries may be used to open the windows 107. FIG. 1C is a zoomed in view to show that even with e-beam resolution lithography, line edge roughness (LER) is nearly 20 nm. The line edge roughness (LER) is corrected in the following fabrication process. Another lithography technique can be used to correct the LER.

FIG. 2 is a perspective view of the intermediate structure 100 illustrating that the exposed (silicon) substrate 110 in the window regions 107 is wet or RIE etched to form (Si) trenches 205. The sidewalls 210 of these trenches 205 determine the location of the nanogaps in later fabrication processes. Each trench has a pair of sidewalls 210, and a back wall. The pair of sidewalls 210 of each individual trench 205 symmetrically tilt outward at the same magnitude, but one angled/tapered sidewall tilts at a positive angle (measured clockwise) and the other angle/tapered sidewall tilts at a negative angle (measured counterclockwise). For example, if the one tapered sidewall 210 is titled 30 degrees, the other tapered sidewall 210 is tilted at −30 degrees (e.g., 330 degrees), thus allowing the pair of sidewalls 210 for the trench 205 to be oppositely symmetric.

In one implementation, a tetramethylammonium hydroxide (TMAH) wet etch was performed to anisotropically etch the Si trenches 205. Etched trenches on the <100> silicon layer bounded by converging <111> planes have an angle of 54.74° with the <100> surface. According to an embodiment, the benefit of an anisotropic wet etch is a retarded etch rate in the <111> direction, meaning that line edge roughness vanishes. Even crudely defined oxide windows result in trench features with nearly atomically smooth sidewalls 210, according to an embodiment.

FIG. 3 is a perspective view of the intermediate structure 100 illustrating that a sacrificial layer 305 is grown in the trench regions 205. The sacrificial layer 305 is what defines the gap width of the fluidic structure. The sacrificial layer 305 may be a thin thermal $SiO_2$ layer. The sacrificial layer 305 covers the bottoms and sidewalls 210 of the trenches 205. The sacrificial layer 305 covering the sidewalls 210 has the same angle (tilt) as the tapered sidewalls, and this angle is to be transferred to the nanogaps below.

In one implementation of fabricating the sacrificial layer 305, a dry oxidation process was employed to conformally grow a high-quality 10 nm layer of $SiO_2$ on the trench faces (i.e., the bottoms and sidewalls). Thin $SiO_2$ layers from 2-10 nm can be routinely grown with a +/−10% tolerance in the thickness target. The uniformity of the silicon oxide is the basis for producing consistent gap sizes well below even the theoretical limit of e-beam lithography capabilities. Thus, embodiments can produce nanogaps and then use state-of-the-art scaling capabilities in a reproducible fashion over a wafer scale in a cost effective manner.

Other sacrificial deposition options for fabricating the sacrificial layer 305 may include atomic layer deposition (ALD), and/or epitaxy, including semiconductor materials.

FIG. 4 is a perspective view of the intermediate structure 100 illustrating that the trenches 205 are filled in with a filling material 405. The filling material 405 may be polycrystalline or polysilicon (poly-Si) or amorphous silicon (a-Si). The filling material 405 (e.g., polysilicon) is deposited in the trenches 205 to backfill these features, preparing them for planarization. This filling material 405 creates a second wall on the exposed side of the sacrificial $SiO_2$ layer (sacrificial layer 305). Together the bulk Si and the poly-Si fill form walls on either side of the sacrificial $SiO_2$ layer located on the sidewalls of the trenches. In other words, the sacrificial layer 305 is sandwiched in between the substrate sidewalls 210 and the polysilicon sidewalls (filling material 405).

In one implementation, low pressure chemical vapor deposition (LPCVD) was used to deposit several hundred nanometers of poly-Si (as the filling material 405), backfilling the 250 nm deep trenches formed by TMAH etching. Although other options may exist for filling the trenches, poly-Si was chosen as the filling material 405 in this implementation for two primary reasons: 1) poly-Si has the ability to be highly selectively polished compared to the $SiO_2$ hard mask 105, and 2) poly-Si can form a native oxide similar to the Si bulk. Having poly-Si form a native oxide similar to the Si bulk is beneficial in microfluidics for easier wetting of the gap feature (i.e., nanogap) that is formed once the sacrificial $SiO_2$ is removed from the trench sidewalls.

FIG. 5 is a perspective view of the intermediate structure 100 illustrating a first chemical mechanical polishing (CMP) process. The first chemical mechanical polishing (CMP) process is used to planarize the filling material 405 (e.g., poly-Si) just back below the hard mask 105 ($SiO_2$) surface, stopping on the hard mask 105.

According to an embodiment, an RDB1001 high rate poly-Si CMP process was carried out to planarize the poly-Si down to the $SiO_2$ hard mask with a significant over-polish margin. Post-polish atomic force microscopy (AFM) scan indicated that the poly-Si is recessed below the surface of the 50 nm thick $SiO_2$ hard mask.

One aspect of the first CMP polish is near zero oxide rate polishing, permitting small and large area features to be flattened and smoothed evenly. Here, the first CMP polish is working to polish away the poly-Si in the field areas and land/stop on the oxide hard mask 105. To accomplish this, RDB1001 (Dow Electronic Materials) is used. The RDB1001 is an alkaline, colloidal silica slurry with low abrasive concentration (approximately (~) 25 micrometer (um) size particles) and is highly selective to poly-Si.

Figure 6A:
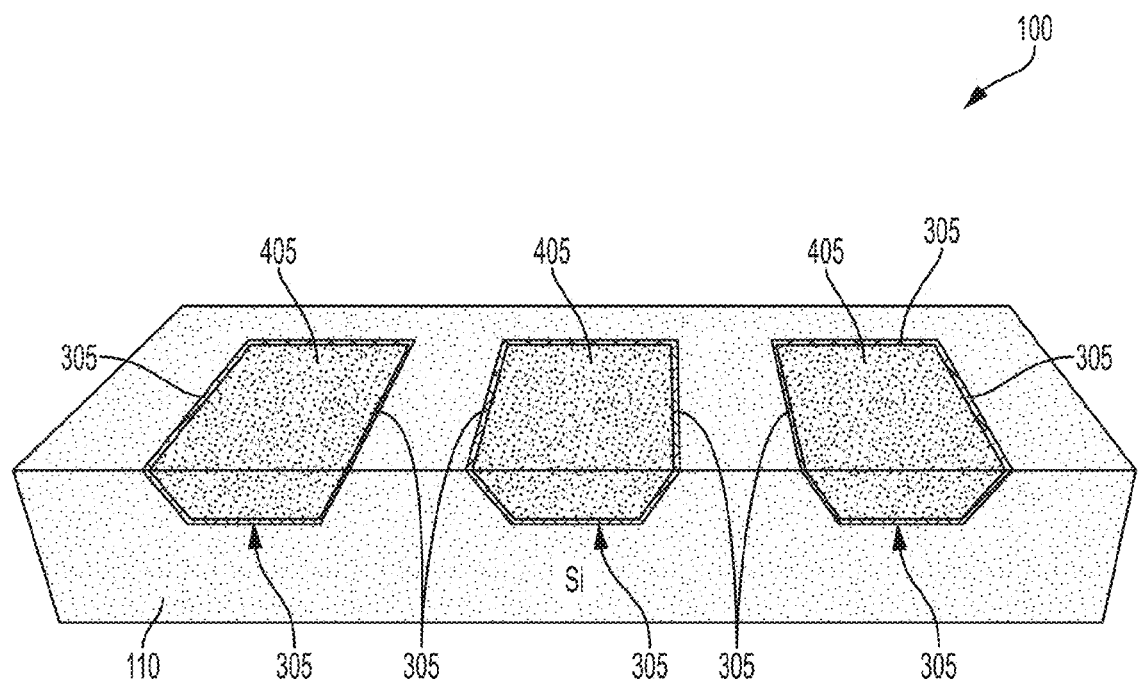
FIG. 6A is a perspective view of the intermediate structure illustrating a second chemical mechanical polishing process according to an embodiment.

FIG. 6A is a perspective view of the intermediate structure 100 illustrating a second chemical mechanical polishing (CMP) process. The second chemical mechanical polishing process is utilized to remove the hard mask 105 (e.g., $SiO_2$ hard mask) and to eliminate poly-Si dishing and roughness (in the filling material 405) from the first polish.

Dishing is defined as the difference in height between the center of the material line (i.e., the lowest point of the dish) and the point where the material levels off (i.e., the highest point of the material). In the filling material 405, there is dishing because the filling material 405 is deeper in the center and protrudes along the boundary/edges.

In one implementation, a 60 second touchup with Ceria STI2100F (with a 6:1 ratio of deionized water to Ceria) removed roughness as well as the poly-Si dish protrusion above the bulk Si surface (i.e., above the substrate 110). It is noted that the ratio of deionized water to Ceria is a mix that has different relationships based on the type of oxide, poly-Si, etc.

Figures 1, 7B:
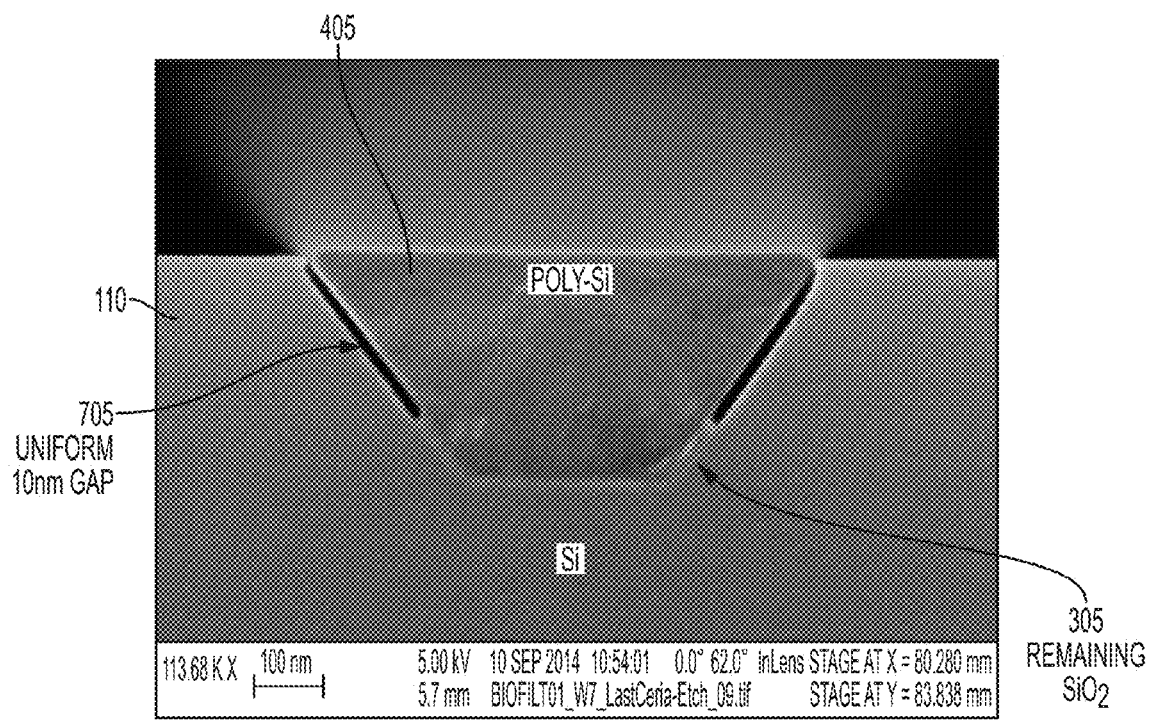
Figures 2, 7B:
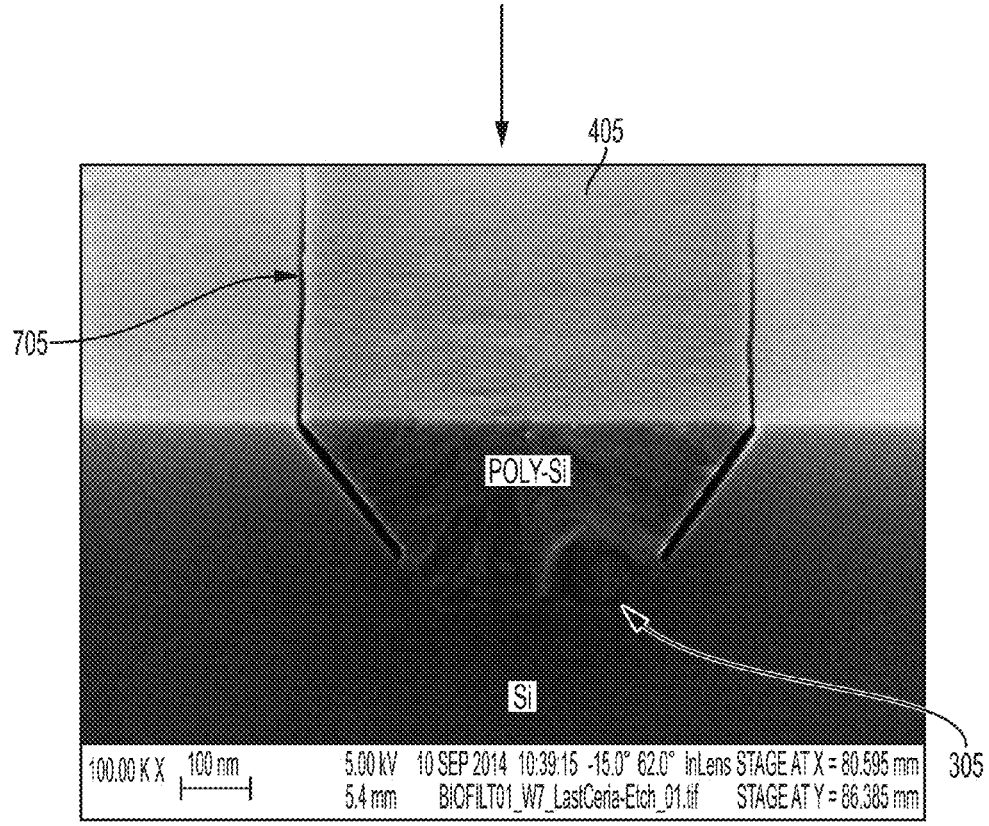
Figure 8A:
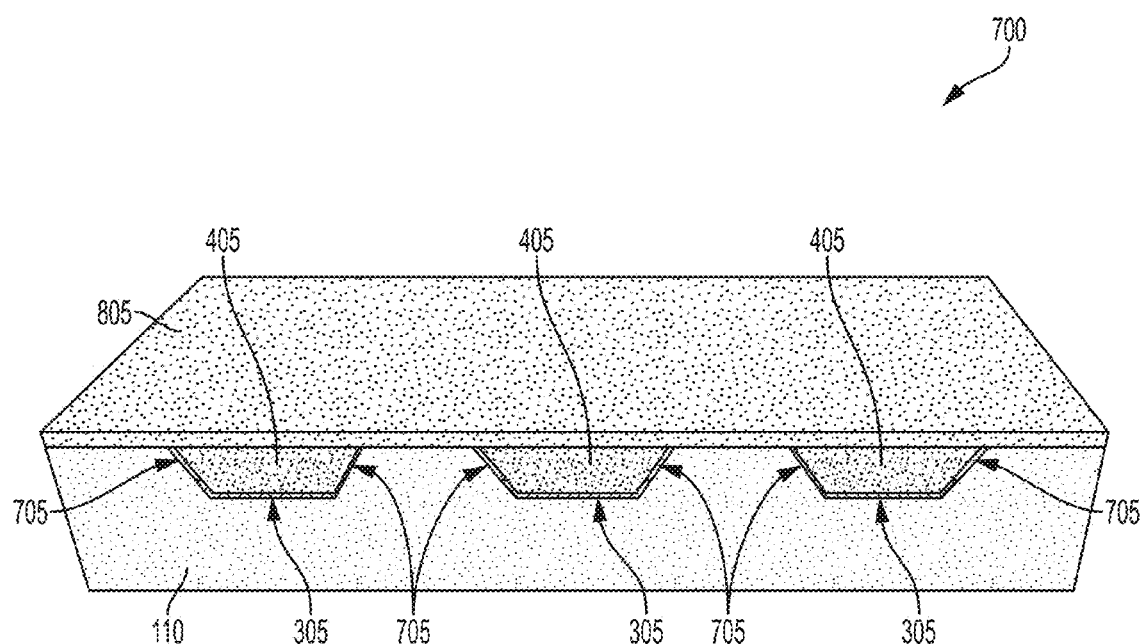
FIG. 8A is a perspective view of the nanochannel/nanogap array structure illustrating that a capping layer seals the nanogaps according to an embodiment.
Figure 8B:
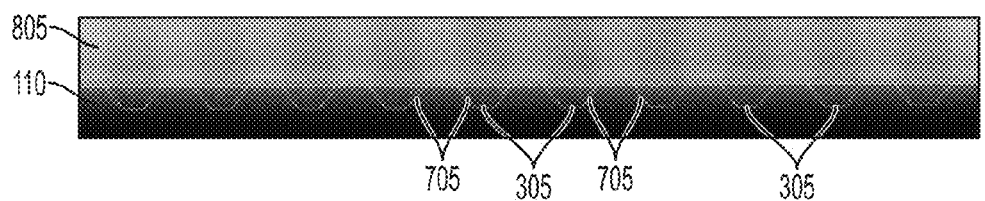
FIG. 8B is a scanning electron microscope image illustrating an array of nanogaps according to an embodiment.
Figure 8C:
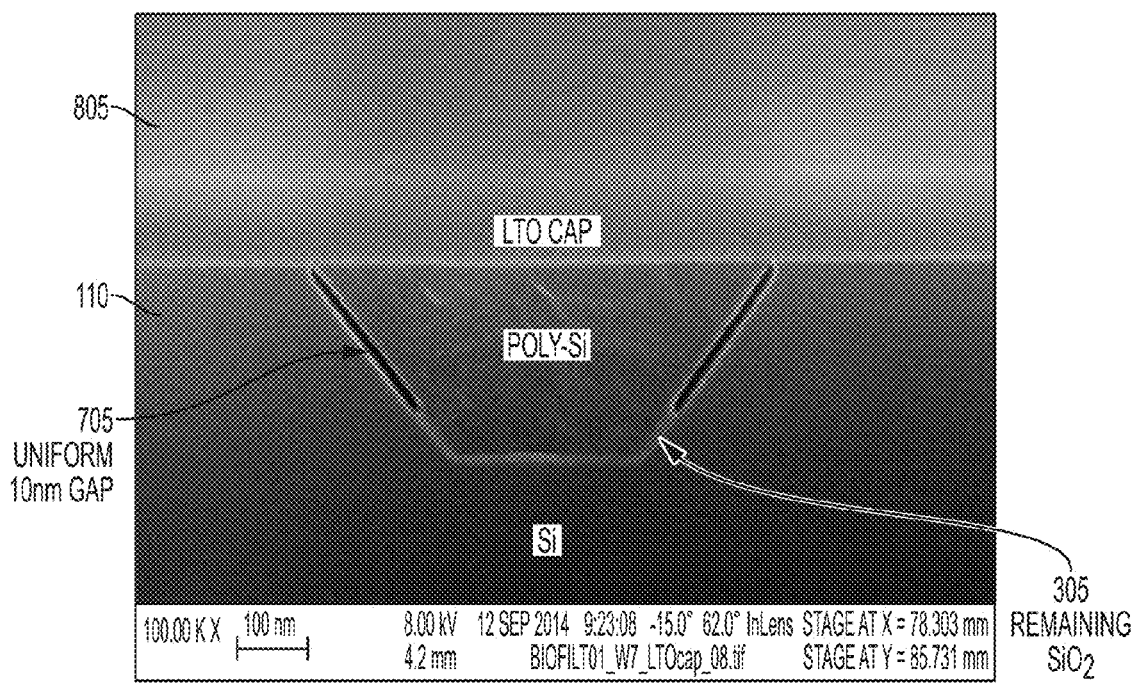
FIG. 8C is a scanning electron microscope image illustrating a cross-sectional view of the nanochannel/nanogap array structure according to an embodiment.

The line edge roughness (LER) present in the $SiO_2$ hard mask 105 is corrected by the TMAH etch process as revealed in FIGS. 6B-1 and 6B-2, where the $SiO_2$ has been removed. FIG. 6B-1 is a cross-sectional view illustrating the dishing and protrusions that need to be removed. FIG. 6B-2 is a top-down view illustrating some correction to the line edge roughness. It is noted that the scanning electron microscope images correspond to the two-step polishing process. Outside of the sequential order for the exemplary fabrication process, FIGS. 6B-1 and 6B-2 show that the sacrificial nanogap oxide is partially removed to make clear the silicon/poly-Si boundaries which would not be performed at this stage in the actual process flow. Etching the oxide in this way also reveals the LER that was present in the oxide. The poly-Si in FIG. 6B-2 has made a mold of the oxide hard mask ledge. The wavy part is the LER mold of the oxide while the straight border around the wavy part is the TMAH corrected border from the silicon etch.

FIG. 6B-3 is a cross-sectional view and FIG. 6B-4 is a top-down view showing a smooth poly-Si surface with the protrusions polished away following the touchup Ceria polish. Unlike the schematic representation in FIG. 6A, the sacrificial layer 305 has already been removed in the SEM images shown in FIGS. 6B-1, 6B-2, 6B-3, and 6B-4.

Further regarding the second chemical mechanical polishing process, Ceria STI2100F may be used for the second polish to remove the 50 nm thick oxide hard mask and to smooth the poly-Si in the trenches and any dishing in the poly-Si. This is a second step shallow trench isolation (STI) slurry that is highly selective to oxide mixed in concentration to create an optimum oxide with poly-Si selectivity, such that the Si in the field and the poly-Si in the trenches are as coplanar as possible at the end of the second polish.

FIG. 7A is a perspective view of the nanochannel/nanogap array structure 700 with the sacrificial layer 305 removed to form the array of nanogaps 705. For example, the poly-Si surface (i.e., filing material 405) is coplanar with the bulk Si (substrate 110), and the sacrificial $SiO_2$ (i.e., sacrificial layer 305) is removed from the trench sidewalls 210 (shown in FIG. 2), revealing the nanogap 705 with a width determined by the $SiO_2$ thickness.

In one implementation, dilute hydrofluoric acid (10:1) was used to controllably remove most (or all) of the silicon dioxide from the sidewalls, leaving a uniform 10 nm wide gap on the trench sidewalls 210. FIG. 7B-1 is a cross-sectional view of a scanning electron microscope image showing that the nanogap is uniform. In FIG. 7B-1, the nanogap is a 10 nm gap between the sidewall of the bulk silicon 110 and the sidewall of the polysilicon filling material 405. It is noted that both the sidewall of the filling material 405 and the sidewalls 210 of the substrate 110 have the same angle. FIG. 7B-2 is a perspective view of a scanning electron image partially showing the top of the nanogap and the front face of the (nanogap) structure.

The nanogap 705 may have different sizes according to the thickness of the sacrificial layer 305. The width W of the nanogap may range from 1 nm to about 300 nm.

FIG. 8A is a perspective view of the nanochannel/nanogap array structure 700 according to an embodiment. A capping layer 805 is deposited onto the planarized structure to seal the nanogaps 705, covering the top of the substrate 110, top of filling material 405, and top of the nanogaps 705. The nanochannel/nanogap array structure 700 is now ready for further processing based on a target application, e.g., nanochannels for translocating and linearizing DNA, nanosieves arrays in a crossflow filter arrangement for sifting single molecules by size exclusion, etc.

In one embodiment, 100 nm of low temperature oxide (LTO) was deposited (as the capping layer 805) on top of the newly formed gap 705 to provide isolation for fluidic flow. FIG. 8B is a scanning electron microscope image showing an array of nanogaps 705 covered with the capping layer 805. FIG. 8C is a scanning electron microscope image showing a cross-sectional view of the nanochannel/nanogap array structure 700.

Access to the nanochannel 705 for a particular application can be obtained by creating reservoirs containing appropriate features on either side of a trench or trench arrays. Post-fabrication of the nanogap structure may include adding reservoirs of various geometries, possibly containing other nanostructures. The reservoirs may be patterned using a RIE etch, thereby enabling access to the nanogaps for a variety of applications.

It is noted that although silicon may be utilized as the substrate 110, silicon dioxide as the hard mask layer 105, silicon dioxide as the sacrificial layer 305, and polysilicon as the filling material 405, other material(s) may be utilized that allow for the sacrificial layer 305 to be selectively etched away while not etching the substrate 110 and the filling material 405. For example, the sacrificial layer 305 may be aluminum oxide, while the substrate 110 is silicon, the hard mask layer 105 is silicon nitride, and the filling material 405 is amorphous silicon.

Figure 9:
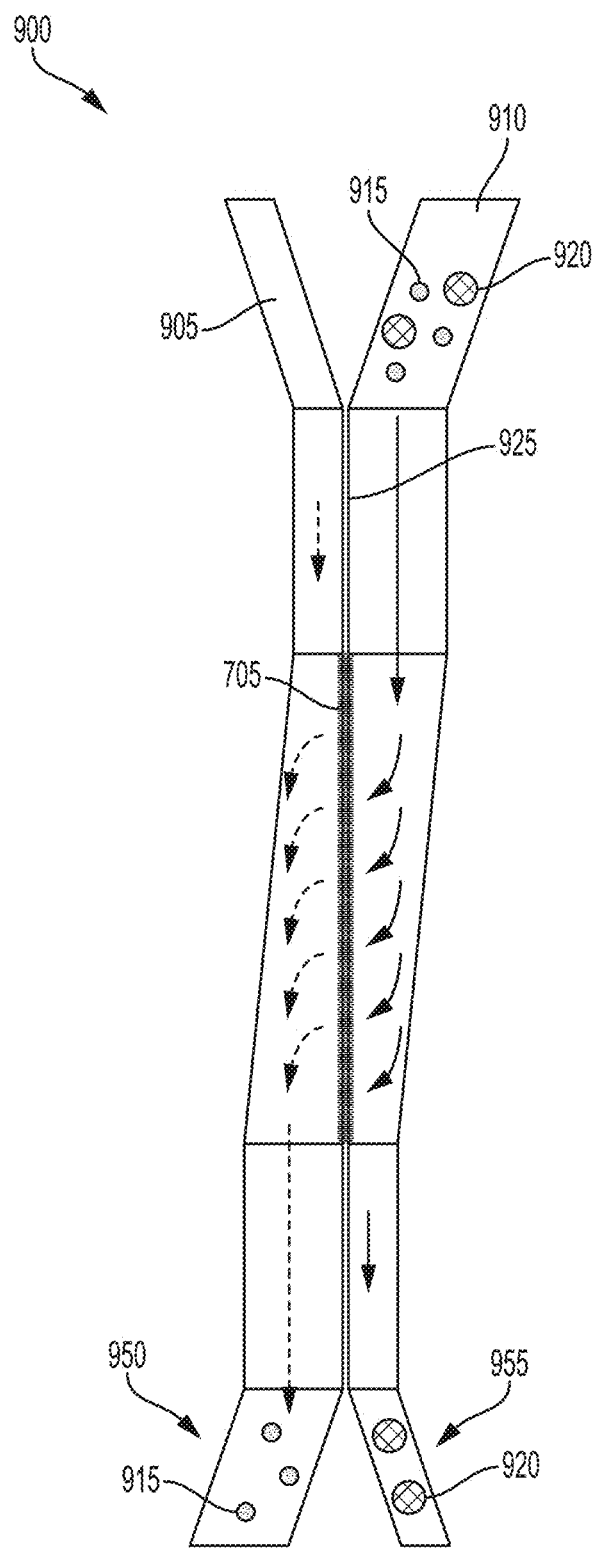
FIG. 9 is a nanosieves system for cross-filter sorting using the nanochannel/nanogap array structure according to an embodiment.

FIG. 9 illustrates a nanosieves system 900 for cross-filter sorting using the nanochannel/nanogap array structure 700 according to an embodiment. The nanosieves system 900 may include a first reservoir 905 (as a buffer inlet) for entering a buffer (e.g., an electrolyte solution) and a second reservoir 910 for entering a combination of particles, e.g., small particles 915 and large particle 920. A thin wall 925 separates the reservoirs 905 and 910. A portion of the thin wall 925 is replaced and/or formed with the nanochannel/nanogap array structure 700 in order to sort the particles 915 and 920.

The large array of nanogaps/nanochannels 705 is formed in or through the thin wall act as sieves to sort particles by size exclusion. The nanogaps/nanochannels 705 are horizontal such that the small particles 915 are sorted to the left side and exit through the left outlet 950, while the large particles 920 cannot flow through the nanogaps/nanochannels 705 and therefore flow to through the right outlet 955.

FIGS. 10A and 10B together depict a flow chart 1000 illustrating a method for nanogap/nanochannel creation according to an embodiment. Reference can be made to FIGS. 1-9.

At block 1005, windows 107 are patterned in a hard mask layer 105 disposed on a substrate 110, as depicted in FIGS. 1A and 1B.

At block 1010, trenches 205 are anisotropically etched trenches in the substrate 110 according to the windows 107 patterned in the hard mask layer 105, such that the trenches 205 have tapered sidewalls 210. Reference can be made to FIG. 2.

At block 1015, a sacrificial layer 305 is formed on the bottoms and the tapered sidewalls of the trenches 205, as depicted in FIG. 3.

At block 1020, a filling material 405 is disposed in the trenches 205 and on top of the hard mask layer 105, where the filling material 405 is on top of the sacrificial layer 305 in the trenches 205. Reference can be made to FIG. 4.

At block 1025, a first chemical mechanical polishing is performed to remove the filling material 405 down to the hard mask layer 105, and the first chemical mechanical polishing is configured to stop on the hard mask layer 105 such that the trenches 205 remained filled with the filling material 405, as depicted in FIG. 5.

At block 1030, a second chemical mechanical polishing is performed to remove the hard mask layer 105, and the second chemical mechanical polishing removes dishing and roughness associated with the filling material 405 in the trenches after the first chemical mechanical polishing. Reference can be made to FIGS. 6A, 6B-3, and 6B-4.

At block 1035, at least a portion of the sacrificial layer 305 is removed from the tapered sidewalls of the trenches 205 such that nanogaps 705 are formed where the sacrificial layer 305 has been removed, while the sacrificial layer 305 remains on the bottoms of the trenches 205. Each of the nanogaps 705 are formed between one tapered sidewall of the substrate 110 and a corresponding tapered sidewall of the filling material 405, and the one tapered sidewall of the substrate 110 opposes the corresponding tapered sidewall of the filling material 405. Reference can be made to FIGS. 7A, 7B-1, and 7B-2.

At block 1040, a capping layer 805 is disposed on top of the substrate 110 and the filling material 405, such that the nanogaps 705 are covered but not filled in as depicted in FIGS. 8A, 8B, and 8C.

The tapered sidewalls 210 of the trenches prevent the capping layer 805 from filling in the nanogaps 705. A nanometer size of the nanogaps 705 further prevents the capping layer 805 from filling in the nanogaps 705. To prevent the nanogap from beginning to file, the upper limit for the nanogap width may be about 50 nm in one implementation although the nanogap 705 may not completely fill in due to the angle of the sidewalls.

An angle of the tapered sidewalls of the trenches 205 prevents the capping layer 805 from filling in the nanogaps 705. The nanogaps are tilted at the (same) angle of the tapered sidewalls of the trenches 205. In one implementation, the angle of the sidewalls 210 (used to form the identical angle of the nanogap) may be about 54.7 degrees which is based on the crystal orientation of, e.g., the silicon substrate.

A width W of the nanogaps 705 corresponds to a thickness of the sacrificial layer 305 formed on the tapered sidewalls 210 of the trenches 205. A width W of the nanogaps is as low as 1 nanometer. The width W of the nanogaps 705 is uniform through a length of the nanogaps 705. The width direction is horizontal (e.g., left and right), the length direction is into the page, and the height is vertical.

A pair of the nanogaps 705 is formed by one trench. The pair, formed by the one trench, is titled away from each other.

Deposition is any process that grows, coats, or otherwise transfers a material onto the wafer. Available technologies include, but are not limited to, thermal oxidation, physical vapor deposition (PVD), chemical vapor deposition (CVD), electrochemical deposition (ECD), molecular beam epitaxy (MBE) and more recently, atomic layer deposition (ALD) among others.

Removal is any process that removes material from the wafer: examples include etch processes (either wet or dry), and chemical-mechanical planarization (CMP), etc.

Patterning is the shaping or altering of deposited materials, and is generally referred to as lithography. For example, in conventional lithography, the wafer is coated with a chemical called a photoresist; then, a machine called a stepper focuses, aligns, and moves a mask, exposing select portions of the wafer below to short wavelength light; the exposed regions are washed away by a developer solution. After etching or other processing, the remaining photoresist is removed. Patterning also includes electron-beam lithography, nanoimprint lithography, and reactive ion etching.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

What is claimed is:

1. A method for gap creation, the method comprising:
   patterning windows in a hard mask layer disposed on a substrate;
   anisotropically etching trenches in the substrate according to the windows patterned in the hard mask layer, such that the trenches have tapered sidewalls;
   forming a sacrificial layer on bottoms and the tapered sidewalls of the trenches;
   disposing a filling material in the trenches and on top of the hard mask layer, the filling material being on top of the sacrificial layer in the trenches;
   performing a first chemical mechanical polishing to remove the filling material down to the hard mask layer, the first chemical mechanical polishing configured to stop on the hard mask layer such that the trenches remained filled with the filling material;

performing a second chemical mechanical polishing to remove the hard mask layer, the second chemical mechanical polishing removing dishing and roughness associated with the filling material in the trenches after the first chemical mechanical polishing;

removing at least a portion of the sacrificial layer from the tapered sidewalls of the trenches such that gaps are formed where the sacrificial layer is removed, while the sacrificial layer remains on the bottoms of the trenches, wherein each of the gaps are formed between one tapered sidewall of the substrate and a corresponding tapered sidewall of the filling material, the one tapered sidewall of the substrate opposing the corresponding tapered sidewall; and disposing a capping layer on top of the substrate and the filling material, such that the gaps are covered but not filled in.

2. The method of claim 1, wherein a width of the gaps corresponds to a thickness of the sacrificial layer formed on the tapered sidewalls of the trenches.

3. The method of claim 1, wherein a width of the gaps is as low as 1 nanometer.

4. The method of claim 1, wherein a width of the gaps is uniform through a length of the gaps.

5. The method of claim 1, wherein the tapered sidewalls of the trenches prevent the capping layer from filling in the gaps.

6. The method of claim 5, wherein a size of the gaps further prevents the capping layer from filling in the gaps.

7. The method of claim 1, wherein an angle of the tapered sidewalls of the trenches prevents the capping layer from filling in the gaps.

8. The method of claim 7, wherein the gaps are tilted at the angle of the tapered sidewalls of the trenches.

9. The method of claim 1, wherein a pair of the gaps are formed by one trench.

10. The method of claim 9, wherein the pair, formed by the one trench, are titled away from each other.

* * * * *